(12) United States Patent
Bemporad et al.

(10) Patent No.: US 8,404,765 B2
(45) Date of Patent: *Mar. 26, 2013

(54) STERICALLY HINDERED AMINES AND USE THEREOF AS POLYMER STABILIZERS

(75) Inventors: Luca Bemporad, Bergamo BG (IT);
Ferruccio Berte, Bergamo BG (IT);
Carlo Seccomandi, Bergamo BG (IT)

(73) Assignee: 3V Sigma S.p.A., Milan MI (IT)

( * ) Notice: Subject to any disclaimer, the term of this patent is extended or adjusted under 35 U.S.C. 154(b) by 478 days.

This patent is subject to a terminal disclaimer.

(21) Appl. No.: 12/702,083

(22) Filed: Feb. 8, 2010

(65) Prior Publication Data
US 2010/0204371 A1 Aug. 12, 2010

(30) Foreign Application Priority Data
Feb. 9, 2009 (IT) .............................. MI2009A0168

(51) Int. Cl.
| | |
|---|---|
| A61K 9/16 | (2006.01) |
| B01F 17/00 | (2006.01) |
| B60C 1/00 | (2006.01) |
| C07D 401/00 | (2006.01) |
| C07D 403/00 | (2006.01) |
| C07D 413/00 | (2006.01) |
| C08G 18/28 | (2006.01) |
| C08G 69/26 | (2006.01) |
| C08G 73/10 | (2006.01) |
| C08K 5/34 | (2006.01) |
| C08K 5/35 | (2006.01) |
| C08K 5/3435 | (2006.01) |
| C08K 5/3492 | (2006.01) |
| C08L 67/00 | (2006.01) |
| C08L 73/00 | (2006.01) |
| C08L 75/00 | (2006.01) |
| C08L 77/00 | (2006.01) |
| C08L 79/00 | (2006.01) |

(52) U.S. Cl. .......... 524/103; 524/97; 524/100; 524/543; 524/570; 524/590; 524/600; 524/601; 524/606; 544/113; 544/198; 544/209; 544/212; 546/187; 546/210

(58) Field of Classification Search .................... 524/97, 524/100, 543, 570, 590, 600, 601, 606, 103; 544/113, 198, 209, 212; 546/187, 210
See application file for complete search history.

(56) References Cited

U.S. PATENT DOCUMENTS
4,331,586 A 5/1982 Hardy
5,180,762 A * 1/1993 Canova .......................... 524/100

FOREIGN PATENT DOCUMENTS
EP 0835873 4/1998
GB 2349642 11/2000
WO 99/29684 6/1999

* cited by examiner

Primary Examiner — Patrick Niland
(74) Attorney, Agent, or Firm — Lucas & Mercanti, LLP

(57) ABSTRACT

The present invention relates to polypiperidine compounds capable of conferring to polymeric materials, particularly polyolefins, a high stability against photodegradation and oxidative action of air, which belong to the HALS category and have the following general formula (I)

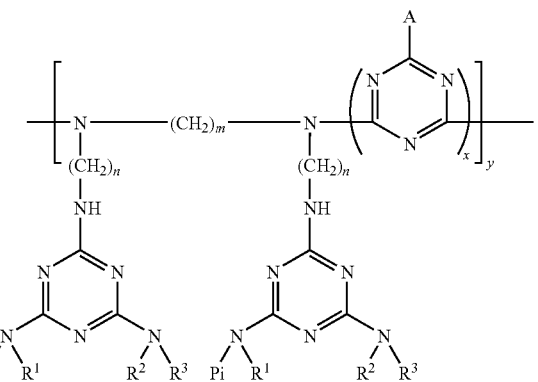

in which x can be zero or 1;
y is between 1 and 10;
m and n, which may be different or equal to each other, range from 2 to 8;
A represents a $NPiR^1$ group or a $NR^2R^3$ group;
and Pi represents the group of formula (II)

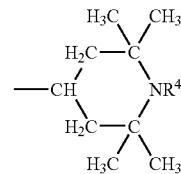

wherein $R^1$ is selected from the group consisting of H, $C_1$-$C_4$ straight-chain and branched-chain alkyl groups;
$R^2$ and $R^3$ can be the same or different and are selected in the group consisting of H, $C_1$-$C_8$ straight-chain and branched-chain alkyl groups, cyclic alkyl groups having from 5 to 12 carbon atoms, or form together with the nitrogen atom a heterocyclic ring having from 5 to 7 members, comprising other heteroatoms such as O,
$R^4$ is selected from the group consisting of H, $C_1$-$C_4$ straight-chain and branched-chain alkyl group, and $OR^5$ group, wherein $R^5$ is selected from the group consisting of H, $C_1$-$C_8$ straight-chain or branched-chain alkyl groups.
The invention also relates to processes for the preparation of the compounds according to the invention.

14 Claims, No Drawings

STERICALLY HINDERED AMINES AND USE THEREOF AS POLYMER STABILIZERS

CROSS REFERENCE TO RELATED APPLICATIONS

This application claims the benefit from Italian Patent Application No. MI2009A000168 filed Feb. 9, 2009, the contents of which are incorporated herein by reference.

FIELD OF INVENTION

The present invention relates to polypiperidine compounds which impart to polymeric materials, in particular to polyolefines, a high stability towards photodegradation and oxidative action of the air. The invention further relates to the processes for preparing the compounds according to the invention.

BACKGROUND OF THE INVENTION

It is known that polymeric materials are subject to deterioration due to the action of heat, light and air, which cause loss of mechanical properties, discoloring and other undesired effects.

Various classes of compounds have been proposed for the stabilization of polymeric materials, principally against UV radiation of the solar light, such as for example benzophenones and benzotriazoles. These compounds confer to the polymers an acceptable stability, which is however not yet sufficient for the practical needs with reference to the fibers, films and raffia made of olefinic polymers.

Polyalkylpiperidine polymers, normally denominated HALS (Hindered Amine Light Stabilizers) are effective for stabilizing polymeric materials and many patents, such as U.S. Pat. No. 4,477,615 and U.S. Pat. No. 4,086,204, describe the preparation and use thereof and the obtained results.

However, said known stabilizers are not completely satisfying and the polymeric materials are still subject to the undesired deterioration due to the action of heat, light and air, with the above mentioned negative consequences. Besides, a further disadvantage of the stabilizer compounds according to the known art is that their synthesis requires the employment of expensive starting compounds which make their preparation costly.

Therefore, there is the need to make available to the industry polypiperidine compounds which can impart to polymeric materials, in particular to polyolefins, a high stability towards photodegradation and oxidative action of the air.

SUMMARY OF THE INVENTION

It is therefore an object of the present invention to provide new polypiperidine compounds capable of conferring to polymeric materials the above mentioned improved stability features. Said object is achieved with polypiperidine compounds whose main features are specified in the first claim, and with the processes for the preparation thereof whose main features are specified in claims 9 and 10. Other features of the invention are disclosed in the remaining claims.

Another object of the invention is to obtain cheaper polypiperidine compounds.

Further advantages and features of the compounds and of the method according to the present invention will become clear to those skilled in the art from the following detailed description and from the accompanying examples of some embodiments thereof.

DETAILED DESCRIPTION OF THE INVENTION

According to the present invention it is possible to confer to polymeric materials a particularly high stability against photodegradation and the oxidative action of air by using HALS having general formula (I):

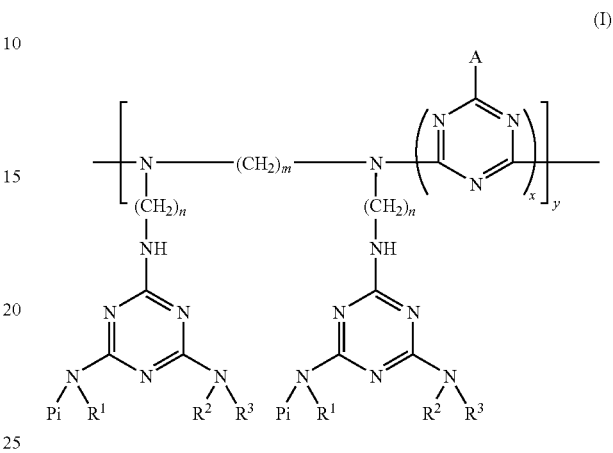

wherein x can be 0 or 1;
y is comprised between 1 and 10;
m and n can be the same or different and are comprised between 2 and 8;
A represents a $NPiR^1$ group or a $NR^2R^3$ group;
Pi represents the following group

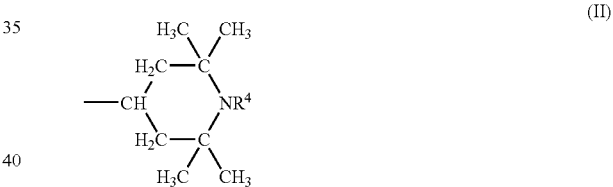

wherein $R^1$ is selected from the group consisting of H, $C_1$-$C_4$ straight-chain and branched-chain alkyl groups;
$R^2$ and $R^3$ can be the same or different and are selected from the group consisting of H, $C_1$-$C_8$ straight-chain and branched-chain alkyl groups, cyclic alkyl groups having from 5 to 12 carbon atoms, or form together with the nitrogen atom a heterocyclic ring having from 5 to 7 members, comprising other heteroatoms such as O,
$R^4$ is selected from the group consisting of H, $C_1$-$C_4$ straight-chain and branched-chain alkyl groups, and $OR^5$ group, wherein $R^5$ is selected from the group consisting of H, $C_1$-$C_8$ straight-chain or branched-chain alkyl groups.

Particularly, the group $NR^2R^3$ may be morpholine.

It has been observed that the compounds of formula (I) wherein m=2 and n=3 are those that confer to the polymeric materials a better stability towards photodegradation and the oxidative action of air.

It has also been found that the stability is further improved when $R^1$ is butyl and a further improvement is obtained if $R^4$ in the Pi group is hydrogen.

Further improvements can be obtained by using the compounds of formula (I) wherein $R^2$ and $R^3$ form, together with the nitrogen atom, a morpholine ring.

Still further improvements of the stability of the polymeric materials can be obtained if x is 0 and y is 1 and the end groups are H and even more with the compounds wherein x is 1 and A is NPiR$^1$ or alternatively if x is 1 and A is NR$^2$R$^3$, wherein R$^1$, R$^2$ and R$^3$ have the above defined meaning.

The compounds of formula (I) can be obtained by a process consisting in reacting an amine having the following general formula

$$NH_2-(CH_2)_n-NH-(CH_2)_m-NH-(CH_2)_n-NH_2 \quad (III)$$

wherein n and m are as above defined,
with a compound having the following general formula

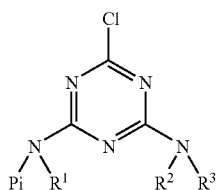
(IV)

wherein Pi, R$^1$, R$^2$ and R$^3$ are as above defined.

Thus, a HALS of formula (I) is obtained, wherein x=0, y=1, the end groups are hydrogen atoms and m, n Pi, R', R$^2$, R$^3$ are as above defined, which can be represented by the following simplified formula:

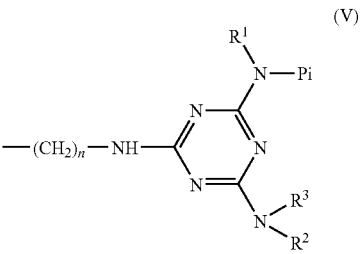
(V)

The HALS of formula (V), being an example of the compounds according to formula (I), is capable of conferring to the polymeric materials a high stability against photodegradation and the oxidative action of air.

An alternative to the above described example is to react the compound of formula (V) with compounds having the following formula:

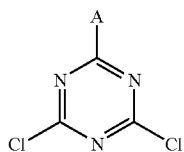
(VI)

wherein A has the above described meaning.

The HALS of formula (V) can be converted into other products comprised in formula (I), wherein x=1, y=1-10 and m, n, P$^1$, R$^I$, R$^2$, R$^3$ have the above defined meanings The end groups of the HALS of formula (I) can be H, OH, OR with R=alkyl or amine group, in particular an amine group derived from formula (V).

The indexes m and n preferably have the meaning of 2 and 3 respectively.

The quantity of HALS according to the present invention which are necessary for an efficient stabilization of the polymeric materials depends on various factors, such as the kind and the features of the polymeric material to be stabilized, the use for which said material is intended, the intensity of the radiations and the period of the foreseen exposure.

In a particular embodiment thereof, the present invention consists in adding to the polymeric material which is to be stabilized the compounds of formula (I) in quantities included between 0.01 and 5% by weight with respect to the polymeric material, preferably from 0.1 to 1.0%. Particularly advantageous results are obtained if the polymeric material is a polyolefine.

In further embodiments of the present invention, the above mentioned composition comprises, as stabilizers for polyolefinic material, further to the HALS of formula (I), other monomeric, polymeric or macromolecular HALS of different nature.

The polymers that can be advantageously stabilized according to the present invention are polyethylene, polypropylene, polystyrene, polybutadiene, polyisoprene, and copolymers thereof, polyvinylchloride, polyvinylidene chloride and copolymers thereof, in particular with ethylene; polyesters such as polyethylenterephtalate; polyamides such as Nylon 6 and 6,6; polyurethanes.

The compounds of the present invention can be incorporated in the polymeric materials with any known method for mixing additives and polymeric materials, for example by means of:

mixing with the polymer, which can be in form of powder of granulate in a suitable mixer for this purpose or an extruder;

adding in the form of a solution or suspension in a suitable solvent and subsequent removal of the solvent from the polymer, which can be in the form of powder, granulate or suspension, after complete mixing;

adding to the polymer during the preparation thereof, for example in the last stage of the preparation.

The compounds of formula (I) can be added to the polymeric material to be stabilized together with, further to the HALS of other type such as above mentioned, also antioxidants based on phenols, amines, phosphites; UV absorbers based on benzophenones, benzotriazoles; nickel stabilizers; plastifiers, lubricants, antistatic agents, flame retardants, corrosion inhibitors, metal deactivators, mineral fillers such as titanium bioxide, aluminum oxide and similar. Some examples of such additives are the following:

A. Antioxidants

1. Alkylated phenols, such as: 2,6-di-tert-butyl-4-methylphenol; 2-(tert-butyl)-4,6-dimethylphenol; 2,6-di-tert-butyl-4-ethylphenol; 2,6-di-tert-butyl-4-butylphenol; 2,6-di-tert-butyl-4-isobutylphenol; 2,6-di-cyclopentyl-4-methylphenol; 2-(α-methylcyclohexyl)-4,6-dimethylphenol; 2,6-di-octadecyl-4-methylphenol; 2,4,6-tricyclohexylphenol; 2,6-di-tert-butyl-4-(methoxymethyl)phenol; linear or branched nonylphenols, such as 2,6-di-cyclononyl-4-methylphenol; 2,4-dimethyl-6-(1'-methylundecyl)phenol; 2,4-dimethyl-6-(1'-heptadecyl)phenol and mixtures thereof.

2. Alkyl-tiomethyl phenols, such as for example 2,4-di-octylthiomethyl-6-tert-butylphenol, 2,4-di-octylthiomethyl-6-methylphenol, 2,4-di-octylthiomethyl-6-ethylphenol, 2,6-di-dodecylthiomethyl-4-nonylphenol.

3. Hydrochinones and alkylated hydrochinones, such as for example: 2,6-di-tert-butyl-4-methoxyphenol; 2,5-di-tert-butyl-hydrochinone; 2,5-di-tert-butyl-hydrochinone; 2,6-diphenyl-4-octadeciloxyphenol; 2,6-di-tert-butyl-hydrochinone; 2,5-di-tert-butyl-4-hydroxyanisole; 3,5-di-tert-butyl-4-hydroxyanisole; 3,5-di-ter-butyl-4-hydroxyphenylstearate; bis(3,5-di-tert-butyl-4-hydroxyphenyl)adipate.

4. Tocopherols, for example α-toeopherol; δ-tocopherol; β-tocopherol; d-tocopherol and mixtures thereof (vitamin E).

5. Hydroxylated thiodiphenyl ethers, such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methyl-phenol); 4,4'-bis[2,6-dimethyl-4-hydroxyphenyl]disulfide.

6. Alkylidene bisphenols, such as 2,2'-methylene-bis(6-tert-butyl-4-methylphenol); 2,2'-methylene-bis(6-tert-butyl-4-ethylphenol); 2,2'-methylene-bis(4-methyl-6-(α-methyl-cyclohexyl)phenol); 2,2'-methylene-bis(4-methyl-6-cyclohexylphenol); 2,2'-methylene-bis(6-nonyl-4-methylphenol); 2,2'-methylene-bis-(4,6-di-tert-butylphenol); 2,2'-ethylidene-bis(4,6-di-tert-butylphenol); 2,2'-ethylidene-bis(6-tert-butyl-4-isobutylphenol); 2,2'-methylene-bis(6-(α-methylbenzyl)-4-nonylphenol); 2,2'-methylenebis(6-(α-α-dimethylbenzyl)-4-nonylphenol); 4,4'-methylenebis(2,6-di-tert-butyl-phenol); 4,4'-methylenebis(6-tert-butyl-2-methyl-phenol); 1,1-bis(5-tert-butyl-4-hydroxy-2-methylphenyl)butane; 2,6-bis(3-tert-butyl-5-methyl-2-hydroxybenzyl)-4-methylphenol; 1,1,3-tris(5-tert-butyl-4-hydroxy-2-methylphenyl)butane; 1,1-bis(5-tert-butyl-4-hydroxy-2-methylphenyl)-3-n-dodecyl-mercaptobutane; ethylene glycol bis-(3,3-bis-(3'-tert-butyl-4'-hydroxyphenyl)-butyrate); bis(2-(3'-tert-butyl-2'-hydroxy-5'-methylbenzyl)-6-tert-butyl-4-methylphenyl)terephthalate; bis(3-tert-butyl-4-hydroxy-5-methylphenyl)dicyclopentadiene; 1,1-bis(3,5-dimethyl-2-hydroxyphenyl)butane; 2,2-bis-(3,5-di-tert-butyl-4-hydroxyphenyl)propane; 2,2-bis-(5-tert-butyl-4-hydroxy-2-methylphenyl)-4-n-dodecyl-mercaptobutane, 1,1,5,5-tetra-(5-ter-butyl-4-hydroxy-2-methylphenyl)pentane.

7. O-, N- and S-benzyl derivates such as: 3,5,3',5'-tetra-ter-butyl-4-4'-dihydroxydibenzyl ether; octadecyl-4-hydroxy-3,5-dimethylbenzyl-mercapto acetate; tridecyl-4-hydroxy-3,5-di-ter-butyl-benzylmercapto acetate; tri(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)disulphide; isooctyl-3,5-di-tert-butyl-4-hydroxybenzylmercaptoacetate.

8. Malonates containing the hydroxybenzyl groups such as; dioctadecyl-2-2,2-bis(3,5-di-tert-butyl-2-hydroxybenzyl)malonate; dioctadecyl-2-(3-tert-butyl-4-hydroxy-5-methylbenzyl)malonate; di-dodecylmercaptoethyl-2,2'-bis-(3,5-di-tert-butyl-4-hydroxybenzyl)malonate; bis-(4-(1,1,3,3-tetramethylbutyl)-phenyl)-2,2-bis-(3,5-di-tert-butyl-4-hydroxybenzyl)malonate.

9. Hydroxybenzyl aromatic compounds, such as 1,3,5-tris-(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; 2,4,6-tris-(3,5-di-tert-butyl-4-hydroxybenzyl)-phenol.

10. Triazine derivates, such as 2,4-bis(octylmercapto)-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)-isocyanurate; 1,3,5-tris-(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris-(3,5-di-tert-butyl-4-hydroxyphenylpropionyl) hexahydro-1,3,5-triazine; 1,3,5-tris-(3,5-dicyclohexyl-4-hydroxybenzyl)isocyanurate.

11. Benzylphosphonates, such as for example: dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-ter-butyl-4-hydroxy-3-methylbenzylphosphonate; calcium salt of the monoethylic ester of 3,5-di-tert-butyl-4-hydroxybenzylphosphonic acid.

12. Acylamino phenols such as lauric acid 4-hydroxyaniline, stearic acid 4-hydroxyaniline, octil N-(3,5-di-tert-butyl-4-hydroxyphenyl)carbamate.

13. β-(3,5-di-tert-butyl-4-hydroxyphenyl)propionic acid esters with mono- or polyhydric alcohols such as; methanol, ethanol, n-octanol, iso-octanol, octadecanol; 1,6-esandiol, 1,9-nonadiol, ethylenic glycol, 1,2-propandiol, neopentyl glycol, thiodiethylene glycol, diethylene glycol, triethylene glycol, pentaerithrol, tri-(hydroxyethyl)isocyanurate; N,N'-bis(hydroxyethyl)oxamide; 3-thioundecanol; 3-thiopentadecanol; trimethyl hexanediol; trimethylolpropane; 4-hydroxymethyl-1-phospho-2,6,7-trioxabicyclo(2,2,2)octane.

14. β-(5-tert-butyl-4-hydroxy-3-methylphenyl)propionic acid esters with mono- or polyhydric alcohols such as; methanol, ethanol, n-octanol, iso-octanol, octadecanol; 1,6-esandiol, 1,9-nonadiol, ethylenic glycol, 1,2-propandiol, neopentyl glycol, thiodiethylene glycol, diethylene glycol, triethylene glycol, pentaerithrol, tri-(hydroxyethyl)isocyanurate; N,N'-bis(hydroxyethyl)oxamide; 3-thioundecanol; 3-thiopentadecanol; trimethyl hexanediol; trimethylolpropane; 4-hydroxymethyl-1-phospho-2,6,7-trioxabicyclo(2,2,2)octane.

15. β-(3,5-dicyclohexyl-4-hydroxyphenyl)propionic acid esters with mono- or polyhydric alcohols such as; methanol, ethanol, n-octanol, iso-octanol, octadecanol; 1,6-esandiol, 1,9-nonadiol, ethylenic glycol, 1,2-propandiol, neopentyl glycol, thiodiethylene glycol, diethylene glycol, triethylene glycol, pentaerithrol, tri-(hydroxyethyl)isocyanurate; N,N'-bis(hydroxyethyl)oxamide; 3-thioundecanol; 3-thiopentadecanol; trimethyl hexanediol; trimethylolpropane; 4-hydroxymethyl-1-phospho-2,6,7-trioxabicyclo(2,2,2)octane.

16. 3,5-di-tert-butyl-4-hydroxyphenyl acetic acid esters with mono- or polyhydric alcohols such as; methanol, ethanol, n-octanol, iso-octanol, octadecanol; 1,6-esandiol, 1,9-nonadiol, ethylenic glycol, 1,2-propandiol, neopentyl glycol, thiodiethylene glycol, diethylene glycol, triethylene glycol, pentaerithrol, tri-(hydroxyethyl)isocyanurate; N,N'-bis(hydroxyethyl)oxamide; 3-thioundecanol; 3-thiopentadecanol; trimethyl hexanediol; trimethylolpropane; 4-hydroxymethyl-1-phospho-2,6,7-trioxabicyclo(2,2,2)octane.

17. β-(3,5-di-tert-butyl-4-hydroxyphenyl)propionic acid amides such as: N,N'-bis(3,5-di-tert-butyl-4-hydroxyphenylpropionil)-hexamethylene diamide; N,N'-bis-(3,5-di-tert-butyl-4-hydroxyphenylpropionyl)-timethylendiamide; N,N'-bis-(3,5-di-tert-butyl-4-hydroxyphenylpropionyl)hydrazide; N,N'-bis(2-(3-(3,5-di-tert-butyl-4-hydroxyphenyl)propionyloxy)ethyl)-oxamide.

18. Ascorbic acid (Vitamin C).

19. Amine antioxidants such as: N,N'-diisopropyl-p-phenylenediamine; N,N'-di-sec-butyl-p-phenylenediamine; N,N'-bis(1,4-dimethyl-pentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis-(2-naphtyl)-p-phenylenediamine; N-isopropyl-N'-phenyl-p-phenylenediamine; N-(1,3-dimethyl-butyl)-N'-phenyl-p-phenylenediamine; N-1-methylheptyl)-N'-phenyl-p-phenylenediamine; N-cyclohexyl-N'-phenyl-p-phenylenediamine; 4-(p-toluensulfamoyl)-diphenylamine; N,N'-dimethyl-N,N-di-sec-butyl-p-phenylendimine; diphenylamine; N-allyl-diphenylamine; 4-isopropoxy-diphenylamine; N-phenyl-1-naphtylamine; N-(4-ter-octylphenyl)-1-naphtylamine; N-phenyl-2-naphtylamine; p,p'-di-ter-octyldiphenylamine; 4-n-butyl-aminophenol; 4-butyryl-aminohenol; 4-nonanoylaminophenol; 4-dodecanoyl-aminophenol; 4-octadecanoyl-aminophenol; bis(4-mothoxyhenyl)amine; 2,6-di-ter-butyl-4-dimethylaminomethylphenol; 2,4'-diaminodiphenylmethane; 4,4'-diaminodiphenyl-methane; N,N,N',N'-tetramethyl-4,4'-diaminodiphenylmethane; 1,2-bis-((2-methylphenyl)amino)ethane; 1,2-bis-(phenylamino) propane; o-tolil-biguanide; bis-(4-(1',3'-dimethylbutyl)phenyl)amine); ter-octyl-N-phenyl-1-naphtylamine; mixtures of dialkylated tert-butyl/tert-octyl-diphenylamines; mixtures of mono- and di-alkyl nonyldiphenylamines; mixtures of mono- and di-alkyl dodecyldiphenylamines; mixtures of mono- and di-alkyl isopropyl/isohexyldiphenylamines; mixtures of mono- and di-alkyl terbutyldiphenylamines; 2,3,dihydro-3,3-dimethyl-4H-1,4-benzothiazine; phenothiazine; mixtures of mono- and di-alkyl tert-butyl/tert-octylphenothiazine; mixtures of mono- and di-alkyl tert-octyl phenothiazine; N-allyl phenothiazine; N,N,N',N'-tetraphenyl-1,4-diamino-2-butene; N,N'-bis-(2,2,6,6-tetramethyl-piperidinyl-4-hexamethylenediamine; bis(2,2,6,6-tetramethyl-piperid-4-yl)sebacate; 2,2,6,6-tetramethyl-piperid-4-one; 2,2,6,6-tetramethyl-piperid-4-ol.

B. UV Absorbers and Light Stabilizers 1. 2-(2'-hydroxyphenyl)benzotriazoles, such as: 2-(2'-hydroxy-5-methylphenyl)benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chloro-benzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)benzotriazole; 2-(2'-hydroxy-4'-octyloxyphenyl)benzotriazole; 2-(3',5'-di-tert-amil-2'-hydroxyphenyl)-benzotriazole; 2-(3',5'-bis-(α,α-dimethylbenzyl)-2'-hydroxyphenyl)benzotriazole; 2-(3'-tert-butyl-5'-(2-(2-ethylhexyloxy)-carbonylethyl)-2'-hydroxyphenyl)-5-chloro-benzotriazole; 2-(3'-tert-butyl-2'-hydroxy-5-(2-octyloxycarbonylethyl)phenyl)-5-chloro-benzotriazole; 2-(3'-tert-butyl-2'-hydroxy-5'-(2-methoxycarbonylethyl)phenyl)-5-chloro-benzotriazole; 2-(3'-text-butyl-2'-hydroxy-5'-(2-methoxycarbonyl-ethyl)phenyl)-benzotriazole; 2-(3'-tert-butyl-2'-hydroxy-5'-(2-octyloxycarbonyl-ethyl)phenyl)-benzotriazole; 2-(3'-tert-butyl-5'-(2-(2-ethylhexyloxy)-carbonylethyl)-2'-hydroxyphenyl)-benzotriazole; 2-(3'-dodecyl-2'-hydroxy-5'-methyl-phenyl)-benzotriazole; 2-(3'-tert-butyl-2'-hydroxy-5'-(2-isooctyloxycarbonylethyl)-phenyl-benzotriazole; 2,2'-methylene-bis-(4-(1,1,3,3-tetramethylbutyl)-6-benzotriazol-2-yl-phenol); the transesterification product of 2-(3'-tert-butyl-5'-(2-methoxycarbonylethyl)-2'-hydroxyphenyl)-2H-benzotriazole with polyethylenglycole 300; (R—CH$_2$—CH$_2$—COO—CH$_2$—CH$_2$—)$_2$— wherein R can be: 3'-tert-butyl-4'-hydroxy-5'-2H-benzotriazole-2-ylphenyl; 2-(2'-hydroxy-3'-(α,α-dimethylbenzyl)-5'-(1,1,3,3-tetramethylbutyl)-phenyl)benzotriazole; 2-(2'-hydroxy-3'-(1,1,3,3-tetramethylbutyl)-5'-(α,α-dimethylbenzyl)phenyl) benzotriazole.

2. 2-hydroxybenzophenones such as for example the 4-hydroxy-; 4-methoxy-; 4-octyloxy-; 4-decyloxy-; 4-dodecyloxy-; 4-benzyloxy-; 4,2',4'-tri-hydroxy- and 2'-hydroxy-4,4'-dimethoxy derivates.

3. Esters of substituted and non-substituted benzoic acids, such as for example: 4-tertbutyl-phenyl-salicylate; phenyl salicylate; octylphenyl salicylate; dibenzoyl resorcinol; bis-(4-tert-butyl-benzoyl)-resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxy-benzoate; 2-methyl-4,6-di-tert-butylphenyl 3,5-di-tert-butyl-4-hydroxybenzoate:

4. Acrilates, such as for example: ethyl α-cyano-β,β-diphenylacrilate; isooctyl α-cyano-β,β-diphenylacrilate; methyl α-carbomethoxycinnamate; methyl α-cyano-β-methyl-p-methoxy-cinnamate; butyl α-cyano-β-methyl-p-methoxy-cinnamate; methyl α-carbomethoxy-p-methoxycinnamate e N-(β-carbomethoxy-β-cyanovinyl)-2-methylindoline.

5. Nickel derivates such as for example: nickel complexes 1:1 or 1:2 with 2,2'-thiobis-(4-(1,1,3,3-tetramethylbutyl)phenol, with or without ligands such as n-butylamine, triethanolamine or N-cyclohexyldiethanolamine; nickel dibutyldithiocarbamate; nickel salts of mono-alkyl esters (for example methyl or ethyl esters) of 4-hydroxy-3,5-di-tert-butylbenzyl-fosfonic acid; nickel complexes of keto-oximes, for example of 2-hydroxy-4-methylphenyl undecyl-keto-oxime; nickel complexes of 1-phenyl-4-lauroyl-5-hydroxy-pyrazole, with or without additional ligands.

6. Sterically hindered amines, such as for example: the condensation product of 2,4-dichloro-6-(4-n-butylamino-2,2,6,6-tetramethyl-4-piperidinyl)-1,3,5-triazine with the condensation product of 2-chloro-4,6-bis-(4-n-butylamino-2,2,6,6-tetramethyl-4-piperidinyl)-1,3,5-triazine with 1,2-bis(3-aminopropylamino)-ethane CAS RN=136504-96-6; bis(2,2,6,6-tetramethyl-4-piperidinyl)sebacate CAS RN=52829-07-9; bis(2,2,6,6-tetramethyl-4-piperidinyl)succinate; bis(1,2,2,6,6-pentamethyl-4-piperidinyl)sebacate CAS RN=41556-26-7; (1,2,2,6,6-pentamethyl-4-piperidinyl)methyl sebacate CAS RN=82919-37-7; bis(1-octyloxy-2,2,6,6-tetramethyl-4-piperidinyl)sebacate CAS RN=129757-67-1; bis(1,2,2,6,6-pentamethyl-4-piperidinyl) n-butyl-3,5-di-ter-butyl-4-hydroxybenzylmalonate; the condensation product of 1-(2-hydroxyethyl)-2,2,6,6-tetramethyl-4-hydroxypiperidine with succinic acid CAS RN=65447-77-0; cyclic or linear condensates of N,N'-bis-(2,2,6,6-tetramethyl-4-piperidinyl) hexamethylenediamine with 4-tert-octylamino-2,6-dichloro-1,3,5-triazine CAS RN=71878-19-8; tris(2,2,6,6-tetramethyl-4-piperidinyl)nitrilotriacetate; tetra(2,2,6,6-tetramethyl-4-piperidinyl)-1,2,3,4-butan-tetracarboxylate; 1,1'-(1,2-ethanediyl)-bis(3,3,5,5-tetramethylpiperazinone); 4-benzoyl-2,2,6,6-tetramethylpiperidine; 4-stearyloxy-2,2,6,6-tetramethyl-piperidine CAS RN=167078-06-0; bis(1,2,2,6,6-pentamethyl-4-piperidinyl)-2-n-butyl-2-(hydroxy-3,5-di-tert-butylbenzyl)malonate CAS RN=63843-89-0; 3-n-octyl-7,7,9,9-tetramethyl-1,3,8-triazaspiro(4,5)decan-2,4-dione; bis(1-octiloxy-2,2,6,6-tetramethylpiperidinyl) sebacate; bis(1-octiloxy-2,2,6,6-tetramethyl-piperidinyl) succinate; linear or cyclic condensates of N,N'-bis-(2,2,6,6-tetramethyl-4-piperidinyl)-hexamethylenediamine with 4-morpholino-2,6-dichloro-1,3,5-triazine CAS RN=82451-48-7; cyclic or linear condensates of N,N'-bis-(1,2,2,6,6-pentamethyl-4-piperidinyl)-hexamethylenediamine with 4-morpholino-2,6-dichloro-1,3,5-triazine CAS RN-193098-40-7; the condensation product of 2-chloro-4,6-bis(4-n-butylamino-2,2,6,6-tetramethylpiperidinyl)-1,3,5-triazine with 1,2-bis(3-amino-propylamino)ethane; the condensation product of 2-chloro-4,6-bis(4-n-butylamino-1,2,2,6,6-pentamethylpiperidinyl)-1,3,5-triazine with 1,2-bis(3-aminopropylamino)ethane CAS RN=106990-43-6; 8-acetyl-3-dodecyl-7,7,9,9-tetramethyl-1,3,8-triazaspiro(4,5)decan-2,4-dione; 3-dodecyl-1-(2,2,6,6-tetramethyl-4-piperidinyl) pyrrolidin-2,5-dione; 3-dodecyl-1-(1,2,2,6,6-pentamethyl-4-piperidinyl)pyrrolidin-2,5-dione; mixture of 4-hexadecyloxy-e 4-octadecyloxy-2,2,6,6-tetramethylpiperidine; the condensation product of N,N'-bis-(2,2,6,6-tetramethyl-4-piperidinyl)hexamethylenediamine with 4-cyclohexylamine-2,6-dichloro-1,3,5-triazine; N-(2,2,6,6-tetramethyl-4-piperidinyl)n-dodecyl succinimide; 2-undecyl-7,7,9,9-tetramethyl-1-oxo-3,8-diazo-4-oxo-spiro(4,5)decane; the condensation product of 7,7,9,9-tetramethyl-2-cyclounaecyl-1-oxo-3,8-diazo-4-oxo-spiro(4,5)decane with epichlorodrine; 1,1-bis(1,2,2,6,6-pentamethyl-4-piperidinyloxicarbonyl)-2-(4-methoxyphenyl)ethene; N,N'-bis-formil-N,N'-bis(2,2,6,6-tetramethyl-4-piperidinyl) hexamethylenediamine diester of 4-methoxy-methylenemalonic acid with 1,2,2,6,6-pentamethyl-4-hydroxypiperidine; poly(methylpropyl-3-oxy-4-(2,2,6,6-tetramethyl-4-piperidinyl))-siloxane; the reaction product of the copolymer maleic acid/alfa-olefins with 2,2,6,6-tetramethyl-4-aminopiperidine or 1,2,2,6,6-pentamethyl-4-aminopiperidine; condensation product of 2-chloro-4,6-bis-(4-n-butylamino-1-cyclohexyloxy-2,2,6,6-tetramethylpiperidinyl)-1,3,5-triaziny with 1,2-bis-(3-amino-propylamino)-ethane; condensation product of 1,6-hexanediamine-bis(2,2,6,6-tetramethyl-4-piperidinyl)- with the condensation product of 2,4,6-trichloro-1,3,5-triazine with di-n-butylamine and N-butyl-2,2,6,6-tetramethyl-4-piperidinamine CAS RN=192268-64-7; derivates of 7-oxa-3,20-diaza-dispiro-(5.1.11.2)-eneicosanone identified by CAS RN 64338-16-5; 85099-51-0; 85099-50-9; 202483-55-4; reaction product of 2,2,6,6-tetramethyl-4-piperidine with the polymer obtainable by copolymerization of maleic anhydride with alkenes C20-24 CAS RN=152261-33-1; products described in EP 782994.

7. Oxamides, such as for example: 4,4'-dioctyloxy-oxanilide; 2,2'-diethoxy-oxalanilide; 2,2'-dioctyloxy-5,5'-di-tert-butyl-oxalanilide; 2,2'-didodecyloxy-5,5'-di-tert-butyl-oxalanilide; 2-ethoxy-2'-ethyloxy-oxalanilide; N,N'-bis(3-dimethylaminopropyl) oxalanilide; 2-ethoxy-2-di-tert-butyl-oxalanilide; mixtures of o- and p-disubstituted methoxy oxalanilides and mixtures of o- and p-disubstituted ethoxy oxalanilides.

8. 2-(2-hydroxyphenyl)-1,3,5-triazines, such as for example: 2,4,6-tris(2-hydroxy-4-octyloxyphenyl)-1,3,5-triazine; 2-(2-hydroxy-4-octyloxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis-(4-methyl-phenyl)-1,3,5-triazine; 2-(2-hydroxy-4-dodecyloxyphenyl)-4,6-bis-(2-4-dimethyl-phenyl)-1,3,5-triazine; 2-(2-hydroxy-4-tridecyloxyphenyl)-4,6-bis-(2-4-dimethyl-phenyl)-1,3,5-triazine; 2-(2-hydroxy-4-(2-hydroxy-3-butyloxy-propoxy)phenyl)-4,6-bis(2,4-dimethyl)-1,3,5-triazine; 2-(2-hydroxy-4-(2-hydroxy-3-octyloxy-propoxy)-phenyl)-4,6-bis(2,4-dimethyl)-1,3,5-triazine; 2-(4-(dodecyloxy/tridecyloxy-2-hydroxypropoxy)-2-hydroxyphenyl)-4,6-bis(2,4-dimethylphenyl)-1,3,5-triazine; 2-(2-hydroxy-4-(2-hydroxy-3-dodecyloxy-propoxy)phenyl)-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris(2-hydroxy-4-(3-butoxy-2-hydroxy-propoxy)phenyl-1,3,5-triazine; 2-(2-hydroxyphenyl)-4-(4-methoxyphenyl)-6-phenyl-1,3,5-triazine; 2-(2-hydroxy-4-(3-(2-ethylhexyl-1-oxy)-2-hydroxypropyloxy)phenyl)-4,6-bis(2,4-dimethylphenyl)-1,3,5-triazine.

C. Metal Deactivators

For example: N,N'-diphenyloxamide; N-salicyilal-N'-salicyloyl-hydrazine; N,N'-bis(salicyloyl)hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxalanilide; isoftaloyl dihydrazide; sebacoyl bisphenylhydrazide; N,N'-diacetyladipoyl dihydrazide; N,N'-bis(salicyloyl)oxalyl dihydrazide; N,N'-bis(salicyloyl)thiopropionyl dihydrazide.

D. Phosphites and Phosphonites

For example: triphenyl phosphite; diphenyl alkyl phosphites; phenyl dialkyl phosphites; tris(nonylphenyl)phosphite; trilauryl phosphite; trioctadecyl phosphite; distearyl pentaerythritol diphosphite; tris(2,4-di-tert-butyl-phenyl) phosphite; diisodecyl pentaerythritol diphosphite; bis(2,4-di-tert-butylphenyl) phosphite; diisodecyl pentaerythritol diphosphite; bis(2,4-di-tert-butylphenyl) pentaerythritol diphosphite; bis(2,6-di-tert-butyl-4-methylphenyl)-pentaerythritol diphosphite; diisodecyloxy-pentaerythritol diphosphite; bis-(2,4-di-tert-butyl-6-methylphenyl)pentaerythritol diphosphite; bis(2,4,6-tris(ter-butylphenyl)pentaerythritol diphosphite; tristearyl sorbitol triphosphite; bis(2,4-di-tert-butyl-6-methylphenyl)methyl phosphite; bis(2,4-di-tert-butyl-6-methylphenyl)ethyl phosphite; 2,2',2"-nitrilo(triethyltris(3,3',5,5'-tetra-tert-butyl-1,1'-biphenyl-2,2'-idyl)phosphite); 2-ethylhexyl (3,3',5,5'-tetra-tert-butyl-1,1'-biphenyl-2,2'-idyl)phosphite); tetra(2,4-di-tert-butylphenyl) 4-4'-biphenylene diphosphonite.

E. Hydroxylamines

For example: N,N-dibenzylhydroxylamine; N,N-diethylhydroxylamine; N,N-dioctylhydroxylamine; N,N-dilaurylhydroxyl-amine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; N,N-dialkylhydroxylamines derived from the hydrogenated tallow amines.

F. Nitrones

For example: N-benzyl-alfa-phenyl-nitrone; N-ethyl-alfa-methyl-nitrone; N-octyl-alfa-eptyl-nitrone; N-lauryl-alfa-undecyl-nitrone; N-tetradecyl-alfa-tridecyl-nitrone; N-hexadecyl-alfa-pentadecyl-nitrone; N-octadecyl-alfa-pentadecyl-nitrone; N-heptadecyl-alfa-heptadecyl-nitrone; N-octadecyl-alfa-hexadecyl-nitrone; nitrones derived from N,N-dialkylhydroxylamines obtained from amines of hydrogenated tallow.

G. Thiosynergic Derivates

For example dilauryl thiodipropionate or stearyl thiodipropionate.

H. Antiperoxide Agents

For example esters of the thiodipropionic acid with lauryl, stearyl, miristic or tridecyl alcohols; mercaptobenzimidazole or 2-mercapto-benzimidazole zinc salt; zinc dibutyldithiocarbamate; dioctadecyl disulphide; pentaerythritol tetrakis(β-dodecylmercapto)propionate.

I. Polyamide Stabilizers

For example copper salts in combination with iodides and/or phosphorated compounds and bivalent manganese salts.

L. Basic Co-Stabilizers

For example: melamine; polyvinylpolypyrrolidone; dicyandiamide; triallylcyanurate; urea derivates; hydrazine derivates; amines; polyamides; polyurethanes; alkaline metal and alkaline-earth metal salts of long-chain fatty acids such as calcium stearate, zinc stearate, magnesium behenate, magnesium stearate, sodium ricinoleate, potassium palmitate, pyrocathecol antimonium or zinc salts.

M. Nucleating Agents

For example: inorganic substances such as talc; metal oxides such as titanium dioxide or magnesium oxide; phosphates, carbonates or sulphates of earth-alkaline metal salts; organic compounds such as mono or polycarboxylic acids and salts thereof, such as 4-ter-butylbenzoic acid, adipic acid, diphenylacetic acid, sodium succinate; sodium benzoate; polymeric compounds such as anionic copolymers.

N. Benzofuranones and Indolinones

For example the ones described in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839; EP-A-0591102; 3-(4-(2-acetoethoxy)phenyl)-5,7-di-ter-butyl-benzofuran-2-one; 5,7-di-ter-butyl-3-(4-(2-stearoyloxyethoxy)phenyl)benzofuran-2-one; 3,3'-bis(5,7-di-ter-butyl-3-(4-(2-hydroxyethoxy)phenyl)benzofuran-2-one); 5,7-di-ter-butyl-3-(4-ethoxyphenyl)benzofuran-2-one; 3-(4-acetoxy-3,5-dimethylphenyl)-5,7-di-ter-butyl-benzofuran-2-one; 3-(3,5-dimethyl-4-pivaloyloxyphenyl)-5,7-di-ter-butyl-benzofuran-2-one; 3-(2,3-di-methylphenyl)-5,7-di-ter-butyl-benzofuran-2-one.

O. Fillers and Reinforcing Agents

For example: calcium carbonate; silicates; glass fibers; asbestos; talc; kaolin; mica; barium sulphate; metal oxides and hydroxides, carbon black; graphite; wood flour or fiber or other natural products; synthetic fibers.

P. Other Additives

For example plastifiers, lubricants, emulsifiers, pigments, rheology modifiers; catalysts; flow control agents; optical bleach; antiflame agents; antistatic agents, swelling agents.

The invention will be further described in greater detail with reference to the following examples:

Example 1

A HALS having structure (I) with $m=2$, $n=3$, $x=0$, $y=1$, $R^1$=n-butyl, Pi-2,2,6,6-tetramethyl-4-piperidine residue, $NR^2R^3$=morpholine residue and end groups being H was prepared according to the following procedure: 0.2 moles of cyanuric chloride were solved in 280 ml of xylene. After cooling to 10° C., 0.2 moles of N-(2,2,6,6-tetramethyl-4-piperidinyl)-butylamine were added in 30 minutes under stirring, maintaining the temperature between 10° C. and 15° C. Then, 46 g of water and 0.216 moles of sodium hydroxide as 30% aqueous solution were added. The solution was heated under stirring up to 60° C., maintaining this temperature for 30', then the aqueous phase was removed. The solution was cooled to 0° C. and 0.2 moles of morpholine were dripped in 30', by maintaining the temperature between 0 and 5° C. At the end of the addition the mixture was heated at 70-80° C. and after 30' stirring, 46 g of water were added and 0.216 moles of sodium hydroxide were added as 30% water solution. After 30' at 85° C. stirring was interrupted and the water phase was removed.

The obtained xylene solution, containing 0.2 moles of a compound of general formula (IV) with $R^1$=n-butyl, Pi=2,2,6,6-tetramethyl-4-piperidine residue, $NR^2R^3$=morpholine residue, was additioned with 0.1 moles of N,N'-bis(aminopropyl)-ethylendiamine, corresponding to an amine having general formula (II) with $m=2$ and $n=3$; the acidity was neutralized with the equivalent quantity of alkali and the solution was boiled, while the formed water was removed by distillation. After all the water was collected, the distillation was continued thus gradually reaching 140° C. in the boiler and by collecting about 110 ml of xylene in three hours. Cooling to 80° C. was performed, 120 ml of water were added and after 30' stirring at 80-90° C. the water phase was discharged.

Thus, 241 g of a xylene phase were obtained which, after filtration for removing possible suspended particles, was dried by distillation of the solvent under vacuum, thus obtaining by cooling of the melt 92 g of solid product (HALS1).

Example 2

A HALS formed of a mixture of oligomers having structure (I) with $x=1$, $y=1$, $m=2$, $n=3$, $R^1$=n-butyl, Pi=2,2,6,6-tetramethyl-4-piperidine residue, $NR^2R^3$=morpholine residue and A=N-(2,2,6,6-tetramethyl-4-piperidinyl)-butylamine was prepared according to the following procedure.

In a reactor, at the temperature of 15-20° C., 0.08 moles of N-(2,2,6,6-tetramethyl-4-piperidinyl)-butylamine were dripped in a solution of 0.08 moles of cyanuric chloride in 156 ml of xylene. After neutralizing with the equivalent quantity of alkali, the water phase was removed, thus obtaining a xylene solution of 0.08 moles of a compound having formula VI with A=residue of N-(2,2,6,6-tetramethyl-4-piperidinyl)butylamine.

Separately, with the same procedure as described in previous example 1, 240 ml of xylene solution were prepared containing 0.1 mol of the compound of formula (V) denominated HALS1.

The two solutions were combined and the resulting mixture was heated to reflux for 5 hours in the presence of 0.17 moles of 30% sodium hydroxide, thus removing the reaction water by distillation.

The solution was then cooled to 80° C., washed with 140 ml of distilled water and, after filtration for removing possible suspended parts, was dried by distillation of the solvent under vacuum, thus obtaining by cooling of the melt 115 g of solid product (HALS2).

Example 3

A HALS formed of a mixture of oligomers having structure (I) with $x=1$, $y=1-10$, $m=2$, $n=3$, $R^1$=n-butyl, Pi=2,2,6,6-tetramethyl-4-piperidine residue, $NR^2R^3$=morpholine residue and A=morpholine residue was prepared according to the following procedure.

In a reactor, at the temperature of 0-5° C., 0.08 moles of morpholine were dripped in a solution of 0.08 moles of cyanuric chloride in 156 ml of xylene. After neutralizing with the equivalent quantity of alkali, the water phase was removed, thus obtaining a xylene solution of 0.08 moles of a compound having formula VI with A=residue of morpholine.

Separately, with the same procedure as described in previous example 1, 240 ml of xylene solution were prepared containing 0.1 mol of the compound of formula (V) denominated HALS1.

The two solutions were combined and the resulting mixture was heated to reflux for 5 hours in the presence of 0.17 moles of 30% sodium hydroxide, thus removing the reaction water by distillation.

The solution was then cooled to 80° C., washed with 140 ml of distilled water and, after filtration for removing possible suspended parts, was dried by distillation of the solvent under vacuum, thus obtaining by cooling of the melt 105 g of solid product (HALS 3).

Example 4

A practical test was applied in order to evaluate the light stabilization of a polyolefin fiber, in particular a polypropylene fiber. In this example and in the following one, the denomination HALS1, HALS 2 and HALS 3 designate the compounds prepared according to examples 1, 2 and 3, respectively.

1000 parts by weight of powder unstabilized polypropylene homopolymer (fluidity index: about 10-12 g/10' at 230° C.-2.16 kP) were mixed in a laboratory mixer with 0.75 parts of Calcium stearate, 0.5 parts by weight of tris-(2,4-di-tert-butyl-phenyl)phosphite, 0.50 parts by weight of 1,3,5-tris(3,5-di-tert-butyl-4-hydroxybenzyl)isocyanurate and 1.5 parts by weight of stabilizers HALS1, 2 or 3 as indicated in the following Table 1.

The dry mixture was extruded in a lab extruder at 230° C. and granulated.

The granulate was transformed in bulked filament having title 480/60 dtex (stretch ratio 1:3) by spinning, by using a lab extruder at a maximum temperature of 260° C.

The filament was exposed in a Weather-Ometer (WOM Ci65) according to ISO 4892. The light resistance was studied by periodically taking treated samples and by subjecting them to tensile strength tests by breaking load check. The parameter to compare the light resistance of the samples was $t_{50}$ defined as "exposure time in WOM, expressed in hours, for a breaking load equal to 50% of the initial value".

The experimental results are shown in Table 1.

TABLE 1

Light stability of bulked filament PP 480/60 dtex

| Stabilization | $t_{50}$ WOM hours |
|---|---|
| Without light stabilizer | 300 |
| 0.15% HALS 1 | 1270 |
| 0.15% HALS 2 | 1410 |
| 0.15% HALS 3 | 1235 |

Example 5

An applicative test was carried out in order to evaluate the light stabilization of a low density polyethylene film (LDPE).

1000 parts by weight of unstabilized LDPE ((fluidity index: about 0.6 g/10' at 190° C.-2.16 kP) were mixed in a laboratory mixer with 0.30 parts of n-octadecyl-3-(3',5'-di-tert-butyl-4-hydroxyphenyl)-propionate and 1.50 parts by weight of stabilizers HALS 1, 2 or 3 as indicated in the following Table 2.

The dry mixture was extruded in a lab extruder at 230° C. and granulated.

The granulate was transformed in film having final thickness of about 150 μm by means of bubble extrusion with a lab extruder provided with rotating head, at a maximum temperature of 230° C.

Test pieces taken from the above film, after being mounted on suitable supports, were exposed in a Weather-Ometer (WOM Ci35a) according to ISO 4892 (cycle 102/18').

The light resistance was studied by periodically taking treated samples and by subjecting them to carbonyl index check by FT-IR measurements.

The parameter to compare the light resistance of the samples was $t_{0,10}$ defined as "exposure time in WOM, expressed in hours, necessary for growing the carbonyl index to a value 0.10".

The experimental results are shown in Table 2.

TABLE 2

Light stability of blown film LDPE having thickness 150 μm

| Stabilization | $t_{50}$ WOM hours |
|---|---|
| Without light stabilizer | 20 |
| 0.15% HALS 1 | 3750 |
| 0.15% HALS 2 | 3900 |
| 0.15% HALS 3 | 3650 |

The patents mentioned herein are incorporated herein by reference.

The invention claimed is:
1. Stabilizing compounds with general formula (I)

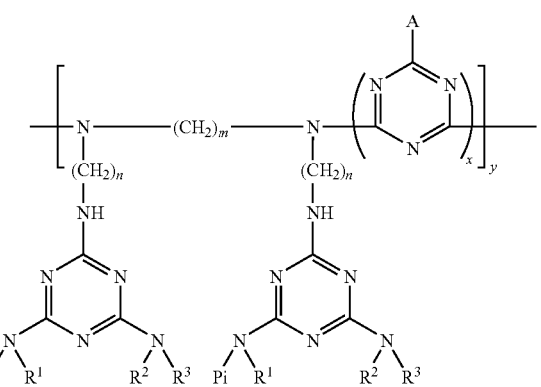

in which x=1;
y is between 1 and 10;
m and n, which may be different or equal to each other, range from 2 to 8;
A represents a NPiR$^1$ group or a NR$^2$R$^3$ group;
and Pi represents the group of formula (II)

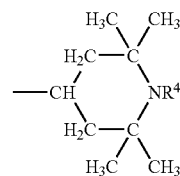

wherein R$^1$ is selected from the group consisting of H, C$_1$-C$_4$ straight-chain and branched-chain alkyl groups;
R$^2$ and R$^3$ can be the same or different and are selected in the group consisting of H, C$_1$-C$_8$ straight-chain and branched-chain alkyl groups, cyclic alkyl groups having from 5 to 12 carbon atoms, or form together with the nitrogen atom a heterocyclic ring having from 5 to 7 members, comprising other heteroatoms;
R$^4$ is selected from the group consisting of H, C$_1$-C$_4$ straight-chain and branched-chain alkyl groups, and OR$^5$, wherein R$^5$ is selected from the group consisting of H, C$_1$-C$_8$ straight-chain or branched-chain alkyl groups
wherein the end groups of the compounds of formula (I) are selected from the group consisting of H, OH, OR wherein R is an alkyl group, and amine groups of formula (V)

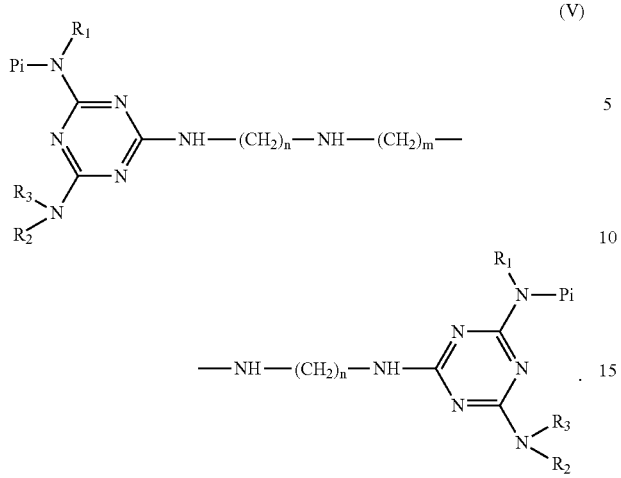

(V)

2. Compounds according to claim 1, in which m=2 and n=3.

3. Compounds according to claim 1, in which $R^1$ is butyl.

4. Compounds according to claim 1, in which in the group Pi, represented by the formula (II), $R^4$=H.

5. Compounds according to claim 1, in which $R^2$ and $R^3$ form together with the nitrogen atom a morpholine ring.

6. Compounds according to claim 1, in which x=0 and y=1 and the end groups are H.

7. Compounds according to claim 1, in which x=1 and A=NPiR$^1$.

8. Compounds according to claim 1, in which x=1 and A=NR$^2$R$^3$.

9. A process for the preparation of compounds having formula (I)

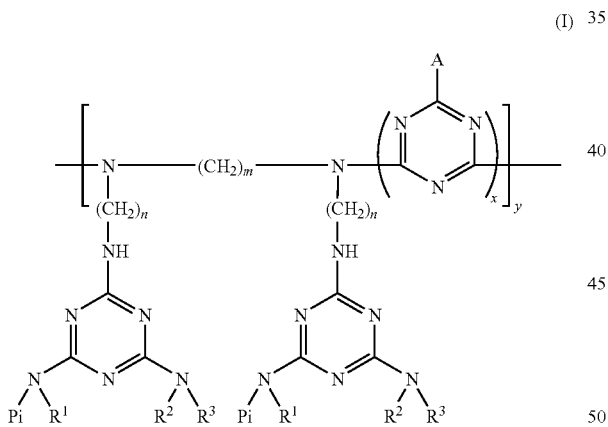

(I)

with x=1 and y=1-10 comprising reacting compounds of the following general formula

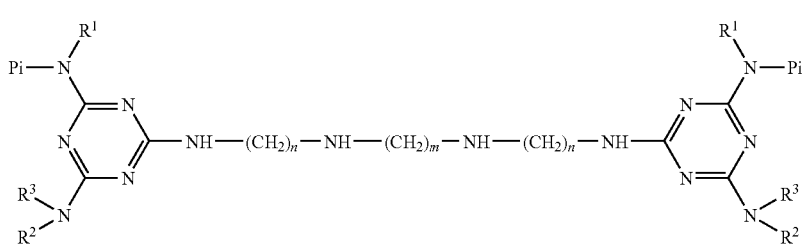

(V)

in which m and n may also be equal to each other, range from 2 to 8 and in which Pi represents a group having the formula

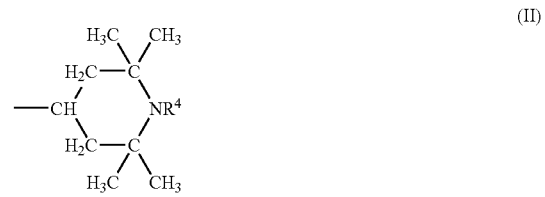

(II)

wherein $R^1$ is selected from the group consisting of H, $C_1$-$C_4$ straight-chain and branched-chain alkyl groups;

$R^2$ and $R^3$ can be the same or different and are selected from the group consisting of H, $C_1$-$C_8$ straight-chain and branched-chain alkyl groups, cyclic alkyl groups having from 5 to 12 carbon atoms, or form together with the nitrogen atom a heterocyclic ring having from 5 to 7 members, comprising other heteroatoms, $R^4$ is selected from the group consisting of H, $C_1$-$C_4$ straight-chain and branched-chain alkyl groups, and OR$^5$, wherein $R^5$ is selected from the group consisting of H, $C_1$-$C_8$ straight-chain or branched-chain alkyl groups, with compounds having the formula (VI)

(VI)

in which A represents a NPiR$^1$ group or a NR$^2$R$^3$ group.

10. A composition comprising a polymeric material and from 0.01% to 5% of a compound according to claim 1.

11. A composition according to claim 10, in which the polymeric material is chosen from the group consisting of polyethylene, polypropylene, polystyrene, polybutadiene, polyisoprene and their copolymers, polyvinyl chloride, polyvinylidene chloride and their copolymers, polyvinyl acetate and its copolymers, polyesters, polyamides, and polyurethanes.

12. A composition according to claim 10, in which the polymeric material is a polyolefin material.

13. A composition according to claim 10, further comprising other monomeric, polymeric or macromolecular HALS.

14. A composition according to claim 1, in which said heteroatom is oxygen.

* * * * *